United States Patent
Monnier et al.

(10) Patent No.: US 11,021,619 B2
(45) Date of Patent: Jun. 1, 2021

(54) IONIC OLIGOMER AND POLYMERIZABLE COMPOSITION CONTAINING SAME FOR TEMPORARY-USE WATER-FRAGMENTABLE MATERIALS

(71) Applicant: Arkema France, Colombes (FR)

(72) Inventors: Guillaume Monnier, Avrigny (FR); Christophe Duquenne, Paris (FR); Sylvain Beaudrais, Agnetz (FR)

(73) Assignee: Arkema France, Colombes (FR)

( * ) Notice: Subject to any disclaimer, the term of this patent is extended or adjusted under 35 U.S.C. 154(b) by 439 days.

(21) Appl. No.: 15/766,862

(22) PCT Filed: Oct. 6, 2016

(86) PCT No.: PCT/FR2016/052583
§ 371 (c)(1),
(2) Date: Apr. 9, 2018

(87) PCT Pub. No.: WO2017/060638
PCT Pub. Date: Apr. 13, 2017

(65) Prior Publication Data
US 2018/0298217 A1    Oct. 18, 2018

(30) Foreign Application Priority Data
Oct. 9, 2015 (FR) ...................................... 1559638

(51) Int. Cl.
| | | |
|---|---|---|
| *C09D 11/101* | (2014.01) | |
| *C09D 4/06* | (2006.01) | |
| *B33Y 70/00* | (2020.01) | |
| *B29C 64/40* | (2017.01) | |
| *C07C 219/08* | (2006.01) | |
| *C08F 20/68* | (2006.01) | |
| *C08G 65/48* | (2006.01) | |
| *C09D 11/102* | (2014.01) | |
| *C09D 11/107* | (2014.01) | |
| *C08F 220/18* | (2006.01) | |
| *B33Y 10/00* | (2015.01) | |
| *B29K 33/04* | (2006.01) | |

(52) U.S. Cl.
CPC ............ *C09D 11/101* (2013.01); *B29C 64/40* (2017.08); *B33Y 70/00* (2014.12); *C07C 219/08* (2013.01); *C08F 20/68* (2013.01); *C08G 65/48* (2013.01); *C09D 4/06* (2013.01); *C09D 11/102* (2013.01); *C09D 11/107* (2013.01); *B29K 2033/04* (2013.01); *B33Y 10/00* (2014.12); *C08F 220/18* (2013.01)

(58) Field of Classification Search
CPC ...... C09D 11/101; C09D 4/06; C09D 11/102; C09D 11/107; B33Y 10/00; B33Y 70/00; B29C 64/40; C07C 219/08; C08F 20/68; C08F 220/18; C08G 65/48; B29K 2033/04
See application file for complete search history.

(56) References Cited

U.S. PATENT DOCUMENTS

| | | |
|---|---|---|
| 5,030,747 A | 7/1991 | Blank et al. |
| 5,792,827 A | 8/1998 | Hintze-Bruning et al. |
| 2012/0157351 A1 | 6/2012 | Webber |
| 2012/0178845 A1 | 7/2012 | Napadensky et al. |
| 2013/0012611 A1* | 1/2013 | Davidson ............... C07C 229/18 522/53 |
| 2013/0090444 A1 | 4/2013 | Horgan et al. |
| 2013/0234370 A1 | 9/2013 | Suzuki et al. |
| 2013/0337277 A1 | 12/2013 | Dikovsky et al. |

FOREIGN PATENT DOCUMENTS

| | | |
|---|---|---|
| CA | 2239310 | 6/1997 |
| CA | 2239439 | 6/1997 |

OTHER PUBLICATIONS

Husemann et al. (Derwent 2004-013601, EP 1348748), 2003.*

* cited by examiner

*Primary Examiner* — Shane Fang
(74) *Attorney, Agent, or Firm* — Christopher Lewis

(57) ABSTRACT

An oligomer bearing at least one crosslinkable ethylenic unsaturation and at least one ionic bond comprises in its structure at least one aminoacrylate group and at least one tertiary amine in a form salified with at least one carboxylic acid. Also described are a process for preparing a solution of the oligomer in a reactive diluent, a crosslinkable composition comprising the oligomer, the use thereof as binder in crosslinkable compositions for temporary-use water-removable materials in coatings, hydrogels and 3D object printing, and the crosslinked material which results from polymerizing the oligomer. As a temporary-use material, the cured oligomer can be easily removed after a temporary function, by simple cleaning with water and optionally at a suitable temperature greater than the glass transition temperature of the crosslinked product.

26 Claims, No Drawings

IONIC OLIGOMER AND POLYMERIZABLE COMPOSITION CONTAINING SAME FOR TEMPORARY-USE WATER-FRAGMENTABLE MATERIALS

CROSS-REFERENCE TO RELATED APPLICATIONS

This application is a U.S. national stage application under 35 U.S.C. § 371 of PCT/FR2016/052583, filed Oct. 6, 2016, which claims the benefit of French patent application number 1559638, filed Oct. 9, 2015.

FIELD OF THE INVENTION

The present invention relates to a specific oligomer bearing at least one crosslinkable ethylenic unsaturation and at least one ionic bond in ammonium carboxylate form, which oligomer comprises in its structure at least one aminoacrylate group and at least one tertiary amine including aminoacrylate, in an ammonium carboxylate salified form salified with at least one carboxylic acid compound. More particularly, the oligomer which is the subject of the present invention results from the linking by ammonium carboxylate ionic bonding between a precursor oligomer bearing said at least one aminoacrylate group and said carboxylic acid compound, which acid compound may be a monoacid or a polyacid and in particular a polyacid which is a diacid, said acid compound possibly being saturated or unsaturated and said precursor oligomer possibly bearing a polymerizable ethylenic unsaturation, in particular acrylate unsaturation, or possibly having no ethylenic unsaturation, with, in this case, the ethylenic unsaturation of the oligomer of the present invention being provided by said carboxylic acid compound.

BACKGROUND OF THE INVENTION

The main objective of the oligomer according to the invention is the use thereof in applications concerning temporary-function or temporary-use materials such as coatings or objects that can be easily removed after a temporary function, by simple cleaning with water or salt water or another aqueous solution, in particular having a pH >7 and preferably >8, more particularly by a water jet and optionally at a suitable temperature greater than the glass transition temperature of the crosslinked product obtained. A particular desired advantage of these functional coatings and articles or parts is that they are friendly to operator health and to the environment in general without the use of dangerous solvents or of corrosive products which can have an effect on health and the environment. More particular targeted applications are also linked to their high water sensitivity and their capacity to form gels in water (hydrogels) that can be used as vectors for various active ingredients in an aqueous medium and that can be easily removed if necessary.

More particularly, the present invention relates to products which are crosslinked from said oligomers according to the invention, with crosslinked products which are water-fragmentable or water-soluble, thus enabling them to be completely removed with water or in an aqueous medium as set out above. In particular, this type of product is of interest in a crosslinkable composition for acting as a support material (also termed sacrificial material) for parts undergoing construction in the 3D printing technique, in particular according to the 3D inkjet/polyjet technique with projection of crosslinkable composition (also termed resin) and curing under radiation, in particular UV radiation, layer by layer. Said support or sacrificial material is subsequently removed by means of simply passing through a bath of water with the pH and the temperature of the bath being adjusted to the technique and to the crosslinkable composition used. In certain cases, it may be necessary to have stirring or a dipping time and/or the presence of additives allowing this removal.

Before crosslinking under radiation and in particular under a UV lamp, the crosslinkable composition comprising said crosslinkable oligomer must have a viscosity of less than 30 mPa·s at the temperature of ejection of said composition, which is typically greater than 45° C. During the manufacturing process, the sacrificial material must provide the characteristics expected of a support, with essentially good mechanical strength so as to satisfy the function of "support" material and a minimum curing (crosslinking) rate under radiation, in particular UV radiation. Preferably, the reactivity corresponds to a curing (or crosslinking) rate equivalent to less than 1 passage at 10 m/min under a UV lamp of 120 Watts/cm for a 25-micron coating. Good dimensional stability with low shrinkage, preferably <1%, may also be of interest.

At the end of the three-dimensional printing, the sacrificial (support) material must dissolve or be removed by water-fragmentation rapidly in water or an aqueous solution without leaving marks on the surface of the 3D object thus produced. The temporary-use material to be sacrificed is water-fragmentable according to the present invention if, after having been placed in water or in a saline or basic aqueous solution (pH>7) with magnetic stirring, the material disintegrates in the form of a "water-dispersible" or "water-soluble" fraction (passing into the aqueous phase after filtration through standard filter paper) and/or a residual solid fraction (after filtration) of homogeneous particle size not exceeding 10 mm. More preferentially, this disintegration produces two fractions as defined above. As test that is suitable for characterizing the degree of water-fragmentability, use may be made of the test as described in the experimental section of the description.

The sacrificial support material surrounding the targeted 3D object has the temporary function of gradually supporting the shape of said article as the number of layers printed and crosslinked one-by-one progresses.

The most common solutions, known from the prior art, of crosslinkable compositions that can serve as "support" material for the layer-by-layer printed 3D object are either based on water-soluble inert material (material that is not reactive under radiation), or based on a polymerizable composition based on radiation-polymerizable water-soluble monoethylenic monomers or oligomers comprising, as essential component, water-soluble inert oligomeric or polymeric components or other water-soluble additives that make it possible to remove the "support" material by dissolving in water.

For example, US 2013/0234370 describes a composition for a water-soluble support material comprising a water-soluble monofunctional polymerizable monomer and a polyoxypropylene glycol of Mn ranging from 100 to 5000 and/or water.

US 2013/0337277 describes a liquid composition for self-destructible temporary structures for a 3D printing process with said composition comprising a copolymer that is biodegradable by enzymatic degradation with activation of a biospecific enzyme after finishing of the 3D object. Said copolymer may comprise polyethylene glycol, polyacrylic acid, polyhyaluronic acid, polycaprolactone or polyvinyl alcohol.

US 2012/0178845 also describes radiation-crosslinkable compositions for 3D printing under radiation and, in particular, a composition that is suitable as a support for the 3D object having as reactive component an acrylic component or a component bearing vinyl ethers or a water-miscible component, which swells in water or in a basic or acidic solution after crosslinking, said component possibly being an acrylated urethane oligomer based on polyethylene glycol or a partially acrylated polyol oligomer or an acrylated oligomer having hydrophilic substituents among amine, hydroxyl or acid. A non-reactive component is also present, chosen from polyethylene glycol (PEG), methoxy PEG, glycerol, polyethoxylated polyol or propylene glycol.

CA 2 239 439 relates to applications other than the printing of 3D objects and describes a process for producing radiation-crosslinkable aqueous paints, which paints are soluble in water and are obtained by mixing a pre-paint A based on a water-immiscible oligomer or polymer binder, bearing at least two ethylenic unsaturations, with a primary-tertiary amine B) at 0.2% to 5% by weight relative to said pre-paint, with incorporation of said amine into said oligomer or polymer, followed by neutralization of the amino groups with an acid and dissolution of the paint in water and adjustment of its viscosity. No mention of the use of such a composition, once crosslinked, as provisional- and temporary-function, and in particular water-removable, material is described or taught.

CA 2 239 310 describes compositions similar to the previous case, aqueous paints, but starting from a water-dispersible or -soluble compatible reactive binder with increase of this compatibility (solubility) by modification of said binder with an amine and neutralization with an acid in order to improve the solubility of the binder of the paint before radiation-crosslinking.

U.S. Pat. No. 5,792,827 describes aqueous compositions of coatings for wood or paper, which are radiation-crosslinkable and based on an adduct of a multifunctional acrylate with an amine. The amines can be neutralized with an acid, such as lactic acid, acetic acid, formic acid or phosphoric acid.

US 2012/0157351 describes a method for inhibiting the formation of hydrated agglomerates in a fluid among water, gas and optionally a liquid hydrocarbon, comprising the addition, to said fluid, of an anti-agglomerating additive or of salts thereof. As additive products, examples include products of addition of dimethylpropylamine or of dibutylpropylamine on 2-ethylhexyl acrylate with salification of the tertiary amine with respectively 1-chlorobutane or with acetic acid. No use in a polymerizable or crosslinkable composition and no use for temporary-function materials is either described or suggested.

SUMMARY OF THE INVENTION

None of the documents cited describes or teaches the principle of the present invention for the obtaining of the temporary-function materials that are easily water-removable as required, either as a support for layer-by-layer (under radiation) 3D-printed objects, or as temporary coatings or as a vector for an active ingredient that is temporary, and also water-removable, and in particular the ingredient of a mixed crosslinked edifice with reversible ionic bonds and linking hydrophilic structures having a viscosity suitable for the application and a mechanical strength sufficient to perform their function of use as temporary material that can be removed with water or with a suitable aqueous solution.

In particular, the composition of the oligomer according to the invention or the polymerizable and in particular crosslinkable composition comprising same, more particularly resulting, by crosslinking, in the 3D object support material, is devoid of any water-soluble free component or free additive that is not reactive by crosslinking, as described in the prior art mentioned above.

The invention relates first to an oligomer which is ionic through bearing at least one ammonium carboxylate ionic bond and which is obtained from a precursor oligomer P comprising at least one aminoacrylate group and from an acid compound which salifies, via said ammonium carboxylate ionic bond, at least one tertiary amine of said oligomer P, which may be an aminoacrylate or optionally another tertiary amine group (amine group or amine function having the same meaning in the subsequent text) borne by an amine compound forming said at least one aminoacrylate group.

The invention also relates to said precursor oligomer P as an intermediate for preparing said oligomer as defined according to the present invention.

Also part of the invention is a solution of said oligomer in a reactive diluent and a polymerizable, in particular crosslinkable, composition comprising at least one oligomer as defined according to the invention.

Another subject of the invention relates to a process for preparing said oligomer, comprising first the preparation of a precursor oligomer P and then its salification, with a carboxylic acid compound in ammonium carboxylate form of at least one tertiary amine of said oligomer P, which may be at least one of said aminoacrylate groups and optionally at least one tertiary amine borne by the starting addition amine forming said aminoacrylate group.

Also part of the present invention is the use of said oligomer or of the solution thereof in a reactive diluent or of a polymerizable, in particular crosslinkable, composition comprising same or of the oligomer as obtained by means of the process described according to the invention, (the use) as a polymerizable and more particularly crosslinkable binder for applications in temporary-function or temporary-use materials that can be removed with water, with a saline aqueous solution or with another aqueous solution which is basic, preferably for coatings, hydrogels or for a support material for a layer-by-layer 3D-printing object.

Finally, the present invention also covers the final, in particular crosslinked, polymer material product obtained by polymerization (polymer) and in particular crosslinking (crosslinked product) of a composition comprising said ionic oligomer.

DETAILED DESCRIPTION OF THE INVENTION

Thus, the first subject of the invention relates to a polymerizable, in particular crosslinkable, oligomer bearing at least one ethylenic unsaturation and at least one ammonium carboxylate ionic bond and comprising in its structure or in its composition:

P) at least one precursor oligomer bearing at least one tertiary amine function in the form of an aminoacrylate group, preferably at least two tertiary amine functions in the form of aminoacrylate groups, resulting from the addition of A) at least one amine compound according to A1) bearing at least one primary amine function (—$NH_2$) and/or secondary amine function (—NH) and optionally at least one tertiary amine function and/or according to A2) bearing at least one secondary amine function (—NH) and optionally at least one tertiary amine function (with the amine compound according to A2) having no primary amine function —NH$_2$), on B) at least one hydrophilic acrylate compound with as a result the formation of said at least one aminoacrylate group, and
C) at least one carboxylic acid compound attached to said precursor oligomer P by at least one ammonium carboxylate ionic bond with at least one of said aminoacrylate groups and optionally (with) at least one of said tertiary amine functions of said amine compound A), said oligomer preferably bearing at least two ammonium carboxylate ionic bonds as defined above.

The term "polymerizable" is intended to mean "able to polymerize through the bearing of at least one polymerizable ethylenic unsaturation" and the term "crosslinkable" is a more specific case of the term "polymerizable" wherein said oligomer "can already crosslink alone and therefore bears at least 2 polymerizable ethylenic unsaturations per molecule". It is obvious that said oligomer, if it is "polymerizable" and "crosslinkable" alone is also respectively "copolymerizable" and "co-crosslinkable" in a composition of "polymerizable" and "crosslinkable" monomers and/or other oligomers.

A "hydrophilic" acrylate means, according to the present invention, that said acrylate is water-soluble or water-dispersible in water without surfactant, also termed "self-dispersible" in water.

According to a first particular option in said oligomer of the invention, said amine compound A) can be selected from:
A1) an amine compound bearing at least one, in particular one, primary amine function, and optionally at least one, in particular one, tertiary amine function and/or at least one, in particular one, secondary amine function, and/or
A2) an amine compound bearing at least one, in particular one, secondary amine function, and optionally at least one, in particular one, tertiary amine function,
and with said acrylate compound B) being at least one multifunctional acrylate compound according to B1) and/or monofunctional acrylate compound according to B2), and in particular in the case where A) is a compound according to A1) or comprises an amine compound according to A1), said acrylate compound B) is a mixture of at least one multifunctional acrylate according to B1) and of at least one monofunctional acrylate according to B2).

More particularly, said hydrophilic acrylate compound B) is a mixture of multifunctional (hydrophilic) acrylate compound according to B1) and of monofunctional (hydrophilic) acrylate compound according to B2).

Said aminoacrylate group of the oligomer of the invention can bear at least one ethylenic unsaturation, in particular acrylate unsaturation, or no ethylenic unsaturation and, in the latter case, said acid compound C) is ethylenically unsaturated.

According to one preferred option of said oligomer, said acid compound C) is a monoacid according to C1) which is ethylenically unsaturated according to C11) and said oligomer bears at least two ammonium carboxylate ionic bonds.

Various options exist for said carboxylic acid compound C). First:
when said carboxylic acid compound C) is according to C1) a monoacid, in this case: C1) can be a monoacid according to C11) which is ethylenically unsaturated and at least one ethylenic unsaturation of said oligomer is borne by at least said monoacid according to C11) by ammonium carboxylate bonding with at least one of said tertiary amine functions among said aminoacrylate groups or optionally among the tertiary amine functions of said amine compound A) and optionally at least one other ethylenic unsaturation of said oligomer is borne by at least one aminoacrylate group in the form of an aminoacrylate-end acrylate group of said precursor oligomer P or C1) can be a monoacid according to C12) which is saturated and at least one ethylenic unsaturation of said oligomer is borne by at least one aminoacrylate group in the form of an aminoacrylate-end acrylate group of said precursor oligomer P, said monoacid according to C1) preferably being according to C11) an unsaturated monoacid and
when said carboxylic acid compound C) is according to C2) a polycarboxylic acid and preferably a diacid, in this case:
C2) can be a polyacid according to C21) which is ethylenically unsaturated, in particular an ethylenically unsaturated diacid, and at least one ethylenic unsaturation of said oligomer is borne by at least said polyacid according to C21) and optionally, in addition, at least one ethylenic unsaturation is borne by at least one aminoacrylate group in the form of aminoacrylate-end acrylate groups of said precursor oligomer P or
C2) can be a polyacid according to C22) which is saturated, in particular a saturated diacid, and said precursor oligomer P bears at least one aminoacrylate-end acrylate group and said resulting oligomer bears at least two acrylate ethylenic unsaturations.

Said "aminoacrylate" group corresponds to the linking group formed during the addition reaction of an "=NH" group of said amine compound A) on an acrylate group $CH_2$=CH—$CO_2$—, with said aminoacrylate group represented by the formula below:

"=N—$CH_2CH_2$—$CO_2$—"     (1)

An "aminoacrylate-end acrylate" group means a residual acrylate group of a multifunctional acrylate according to B1), after formation of an "aminoacrylate" group as explained above with an acrylate group of an acrylate according to B1): ($CH_2$=CH—$CO_2$)$_n$—R of functionality n with respect to acrylates of at least 2, according to the scheme below:

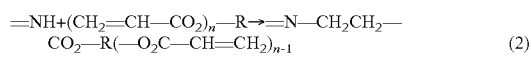

=NH+($CH_2$=CH—$CO_2$)$_n$—R→=N—$CH_2CH_2$—$CO_2$—R(—$O_2C$—CH=$CH_2$)$_{n-1}$     (2)

In the case above, for an =NH addition on an acrylate group, there are n−1 acrylate groups borne by said "aminoacrylate" group and therefore n−1 "aminoacrylate-end acrylate" groups.

According to one preferred option, said carboxylic acid compound C) in said oligomer according to the invention is an unsaturated diacid according to C21) or a saturated diacid according to C22) linking, by two carboxylic ionic bonds, two molecules of said precursor oligomer P, by salification in ammonium carboxylate salt form of one of said tertiary amine functions among said aminoacrylate groups formed, or optionally among said tertiary amine functions of said amine compound A), on each of said molecules of said oligomer P or said carboxylic acid compound C) is a monoacid according to C1), which is ethylenically unsaturated according to C11) and has a polymerizable ethylenic unsaturation, and said monoacid according to C11) salifies at least two of said tertiary amine functions in ammonium carboxylate (ionic bond or salt) form.

More particularly, in the case of a diacid according to C21) or according to C22), said oligomer according to the invention can be represented schematically by general formula (3) below:

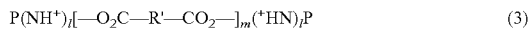

(3)

with R' being ethylenically unsaturated if said acid compound C) is according to C21) and R' being unsaturated if said acid compound C) is according to C22), "l" being the number of ammonium carboxylate sites per molecule of precursor oligomer P and "m" the number of molecules of diacid between two chains (molecules) of precursor P with l=m.

More particularly, in the oligomer according to the present invention, said precursor oligomer P comprises, in its structure, hydrophilic chain segments which can be water-soluble (soluble in water) or water-dispersible (dispersible in water without addition of surfactant), in particular selected from polyethers or from polyesters, in particular polyesters based on oligoether polyols or on ethoxylated polyols, or from polyurethanes based on oligoether polyols or on ethoxylated polyols, in particular from polyurethanes based on oligoether polyols, in particular said segments having a number-average molecular weight Mn of less than 2000, preferably less than 1000. The Mn is in particular calculated from the OH number, $N_{OH}$, of the polyol or monool expressed in mg KOH/g and from its hydroxyl functionality f. The Mn is calculated from:

$$Mn = f \times 56,000/N_{OH}$$

The preferred hydrophilic structure for said precursor oligomer P is polyethers or oligoethers based on polyoxyethylene having an Mn as indicated above.

According to a first more particular option of said oligomer of the invention, depending on the carboxylic acid compound C) chosen, said carboxylic acid compound C) is according to C11) an ethylenically unsaturated monoacid and selected from: acrylic or methacrylic acid, crotonic acid (trans-2-butenoic acid) or β-carboxyethyl acrylate (β-CEA) or mixtures thereof, preferably acrylic or methacrylic acid or β-CEA or mixtures thereof and more particularly acrylic or methacrylic acid or mixtures thereof.

According to another more particular option, said carboxylic acid compound C) is according to C22) a saturated dicarboxylic acid and selected from: succinic acid, malonic acid, malic acid, glutaric acid ($C_5$: bearing 5 carbon atoms), adipic acid ($C_6$), pimelic acid ($C_7$) or acid diesters of abovementioned diacids with a $C_2$ to $C_4$ alkanediol or with a di-, tri- or tetraethylene glycol or diacids among fatty acid dimers and/or trimers, in particular hydrogenated fatty acid dimers and/or trimers ($C_{36}$ dimers and $C_{54}$ trimers), or mixtures thereof, in particular mixtures of two or of three, and preferably from succinic acid, malonic acid, malic acid, glutaric acid ($C_5$) or diacids from fatty acid dimers and/or trimers, in particular hydrogenated fatty acid dimers and/or trimers, or mixtures thereof.

According to a third more particular option, said carboxylic acid compound C) is according to C21) an unsaturated dicarboxylic acid and selected from: itaconic acid, maleic acid, fumaric acid, tetrahydrophthalic acid (cyclohexenedioic acid), or acid diesters of the abovementioned diacids with a $C_2$ to $C_4$ alkanediol or with a di-, tri- or tetraethylene glycol or non-hydrogenated fatty acid dimers and/or trimers ($C_{36}$ dimers and $C_{54}$ trimers), or mixtures thereof, preferably from itaconic acid, maleic acid, fumaric acid and mixtures thereof.

The structure of said oligomer of the invention and in particular the ethylenic unsaturation and Its position will depend on the presence or absence of such an unsaturation in said precursor oligomer P and on the presence or absence of such an ethylenic unsaturation in said carboxylic acid compound C) according to whether it is saturated or unsaturated.

Said precursor oligomer P either bears no aminoacrylate-end acrylate group (no acrylate), or it bears at least one aminoacrylate-end acrylate group (an acrylate) and:
a) in the case where said precursor oligomer P bears an aminoacrylate-end acrylate group:
   a1) said carboxylic acid compound C) is an ethylenically unsaturated monoacid according to C11) or
   a2) said carboxylic acid compound C) is an unsaturated diacid according to C21) or a saturated diacid according to C22), preferably saturated according to C22),
b) in the case where said precursor oligomer P bears no aminoacrylate-end acrylate group, in this case:
   b1) said carboxylic acid compound C) is an unsaturated monoacid according to C11) and two molecules of said monoacid according to C11) are attached to said precursor oligomer P, by two ionic bonds or
   b2) said carboxylic acid compound C) is an unsaturated diacid according to C21) or a saturated diacid according to C22), preferably saturated according to C22) and in the presence of an unsaturated monoacid according to C11) or
   b3) said carboxylic acid compound C) is an unsaturated diacid according to C21).

The functionality of the oligomer of the invention with respect to ethylenic unsaturations will also depend on the presence or absence of ethylenic unsaturation in said precursor oligomer P and said carboxylic acid C). More particularly, the oligomer according to the invention can have an ethylenic unsaturation functionality f as follows:
a') f=1 with said carboxylic acid compound C) being according to C11) an unsaturated monoacid salifying (in ammonium carboxylate salt form) just one of said tertiary amine functions possibly being an aminoacrylate formed in said precursor oligomer P or optionally of the tertiary amine functions borne by said starting amine compound A), said precursor oligomer P bearing no aminoacrylate-end acrylate group (per molecule) or
b') f=2 with:
   said carboxylic acid compound C) being according to C11) an unsaturated monoacid salifying two of said tertiary amine functions possibly being aminoacrylates formed in said precursor oligomer P and/or optionally of the tertiary amine functions borne by said starting amine compound A), said precursor oligomer P bearing no aminoacrylate-end acrylate group (per molecule) or
   said carboxylic acid compound C) being according to C21) a saturated diacid salifying one of said tertiary amine functions possibly being aminoacrylates formed in said precursor oligomer P or optionally of the tertiary amine functions borne by said starting amine compound A) and with two ammonium carboxylate bonds bonding said diacid according to C21) to two molecules of said precursor oligomer P, said precursor oligomer P bearing a single aminoacrylate-end acrylate group (per molecule) or
   said carboxylic acid compound C) being according to C11) an unsaturated monoacid salifying one of said tertiary amine functions possibly being aminoacrylates formed in said precursor oligomer P and/or optionally of the tertiary amine functions borne by said starting amine compound A) and said precursor oligomer P bearing a single aminoacrylate-end acrylate group (per molecule),
c') f=3 with:

said carboxylic acid compound C) being according to C11) an unsaturated monoacid salifying three of said tertiary amine functions possibly being aminoacrylates formed in said precursor oligomer P and/or optionally of said tertiary amine functions borne by said starting amine compound A) and with said precursor oligomer P bearing no aminoacrylate-end acrylate group or said carboxylic acid compound C) being according to C11) an unsaturated monoacid salifying two functions of said tertiary amine functions possibly being aminoacrylates formed in said precursor oligomer P and/or optionally of the tertiary amine functions borne by said starting amine compound A), in ammonium carboxylate form, with said precursor oligomer P bearing a single aminoacrylate-end acrylate group or said acid compound C) being according to C22) an unsaturated diacid salifying one of said tertiary amine functions possibly being aminoacrylates formed in said precursor oligomer P or optionally of the tertiary amine functions borne by said starting amine compound A), in each of two molecules of precursor oligomer P, said precursor oligomer P bearing a single aminoacrylate-end acrylate group per molecule or said carboxylic acid compound C) being according to C11) an unsaturated monoacid salifying one of said tertiary amine functions possibly being aminoacrylates formed in said precursor oligomer P or optionally of the tertiary amine functions borne by said starting amine compound A), with said precursor oligomer P bearing two aminoacrylate-end acrylate groups per molecule or said carboxylic acid compound C) being a mixture of an unsaturated diacid according to C22) and of an unsaturated monoacid C11), with said diacid according to C22) linking by salification two molecules of said precursor oligomer P having each of said molecules, one of said tertiary amine functions possibly being aminoacrylates formed in said precursor oligomer P or optionally of tertiary amine functions borne by said starting amine compound A), salified by said diacid according to C22), and a second of said tertiary amine functions salified by said monoacid according to C11), said (final) oligomer bearing four ammonium carboxylate ionic bonds or said carboxylic acid compound C) being a saturated diacid according to C21) linking by salification two precursor oligomers P, one of which bears an aminoacrylate-end acrylate function (per molecule) and the other of which bears two aminoacrylate-end acrylate functions (per molecule)

d') f=4, with:

said carboxylic acid compound C) being an unsaturated monoacid C11) salifying four of said tertiary amine functions possibly being aminoacrylates formed in said precursor oligomer P and/or optionally of the tertiary amine functions borne by said starting amine compound A), said oligomer P bearing no aminoacrylate-end acrylate group per molecule or said carboxylic acid compound C) being a saturated diacid according to C21) and linking two molecules of said precursor oligomer P by salification of one of said tertiary amine functions possibly being aminoacrylates formed in said precursor oligomer P or optionally of the tertiary amine functions borne by said starting amine compound A), respectively in each of two molecules of said precursor oligomer P, and with said precursor oligomer P bearing 2 aminoacrylate-end acrylate groups per molecule or said carboxylic acid compound C) being a saturated diacid according to C21) and linking two molecules of said precursor oligomer P by salification of one of said tertiary amine functions possibly being aminoacrylates formed in said precursor oligomer P or optionally of the tertiary amine functions borne by said starting amine compound A), respectively in each of two molecules of said precursor oligomer P, and with a first precursor oligomer P bearing 2 aminoacrylate-end acrylate groups per molecule and a second bearing a single aminoacrylate-acrylate group or said carboxylic acid compound C) being an unsaturated monoacid C11) salifying three of said tertiary amine functions possibly being aminoacrylates formed in said precursor oligomer P and/or optionally of the tertiary amine functions borne by said starting amine compound A), with said precursor oligomer P bearing a single aminoacrylate-end acrylate group per molecule or said carboxylic acid compound C) being an unsaturated monoacid C11) salifying two of said tertiary amine functions possibly being aminoacrylates formed in said precursor oligomer P and/or optionally of the tertiary amine functions borne by said starting amine compound A), with said precursor oligomer P bearing two aminoacrylate-end acrylate groups per molecule or said carboxylic acid compound C) is an unsaturated monoacid C11) salifying one of said tertiary amine functions possibly being aminoacrylates formed in said precursor oligomer P or optionally of the tertiary amine functions borne by said starting amine compound A), with said precursor oligomer P bearing three aminoacrylate-end acrylate groups per molecule, with, in the case where a diacid according to C21) or according to C22) is used to link by salification two molecules of said precursor oligomer P, said molecules of said precursor oligomer P possibly being of identical or different structure.

According to one particular option, the components of said precursor oligomer P, that is to say the amine compound A) and/or the hydrophilic acrylate compound B), can be respective mixtures of compounds A) and/or B). Likewise, said precursor oligomer P may be a mixture of precursor oligomers P that are different in terms of structure and in terms of functionality and/or said carboxylic acid compound C) may be a mixture of different carboxylic acids C) (of different structure).

In particular, said amine compound A) may be a mixture of amine compounds A) as defined above and/or said acrylate compound B) may be a mixture of compounds B) as defined above and/or said acid compound C) may be a mixture of compounds C) as defined above. Likewise, said acid compound C) may be a mixture, in particular a mixture of ethylenically unsaturated monoacids according to C11) or a mixture of ethylenically unsaturated diacids according to C21) or a mixture of saturated diacids according to C22) or a mixture of said acids according to C11) and according to C21) and optionally according to C22).

More particularly, said amine compound A) may be a mixture of amine compounds A), as defined above, and in particular a mixture of amine compounds according to A1) or according to A2) or a mixture of amine compounds according to A1) and according to A2), with said compounds according to A1) or according to A2) being as defined according to the invention above. Likewise, the acrylate compound B) may be a mixture of at least one monofunctional acrylate compound, which in particular may be a mixture of monofunctional acrylate compounds and of at least one multifunctional acrylate compound, which in particular may be a mixture of multifunctional acrylate compounds of different chemical nature and of identical or different functionality or of identical nature and different functionality.

In the case of mixtures, the functionality to which reference is made corresponds to the number-average functionality $f_{ave}$ which is calculated according to formula (4) below:

$$f_{ave} = \Sigma_i(n_i * f_i) \quad (4)$$

with $\Sigma_i(n_i)=1$ and $n_i$ being the number-fraction of molecules i of functionality $f_i$.

Said precursor oligomer P can be defined in particular according to general formula (I) below:

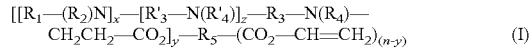

with:
$R_1$, $R_2$ being $C_1$ to $C_4$ alkyls of a different tertiary amine of an aminoacrylate or $R_1$—N= and
$R_2$—N=, being a group encompassing an aminoacrylate bond $R_6$—$O_2CCH_2CH_2N$— and in this case with $R_1$ or $R_2$ identical or different and corresponding to $R_6$—$O_2CCH_2CH_2$, with $R_6$ being the residue of a monoacrylate compound, in particular a polyether diol monoacrylate or a polyether monoalcool monoacrylate.
$R_3$: residue of said amine compound A), if bearing a primary amine function or optionally a tertiary amine function, with z=0 and meaning the absence of secondary amine function in the presence of the primary amine function,
$R'_3$: is, for z=0 and x=1, a single bond between $R_3$ and the tertiary amine group "$R_1$—($R_2$)N—", said amine compound A) bearing a primary amine function and a tertiary or $R'_3$: is a $C_2$ to $C_6$ alkylene for z=1 and x=1 with said amine compound A) bearing a primary amine function, a secondary amine function and a tertiary amine function,
$R_4$: for z=0, is a $C_1$ to $C_4$ alkyl when said amine compound A) bears a secondary amine
function and optionally a tertiary amine function,
if not, when said amine compound A) bears a primary amone function,
in this case
$R_4$: —[$CH_2CH_2$—$CO_2$]$_y$—$R_5$—($CO_2$—CH=$CH_2$)$_{(n-y)}$ or
$R_4$: at least one part is —$CH_2CH_2$—$CO_2$—$R'_5$ when a monofunctional acrylate of radical $R'_5$ is present in addition to the multifunctional acrylate, with $R'_5$ possibly comprising a free hydroxyl group,
$R'_4$: —[$CH_2CH_2$—$CO_2$]$_y$—$R_5$—($CO_2$—CH=$CH_2$)$_{(n-y)}$ when z=1 meaning the simultaneous presence of a primary amine function with a secondary,
$R_5$: residue of said multifunctional acrylate compound B selected in particular from residues of polyethers, of polyesters or from residues of polyurethanes based on polyesters and polyether polyols,
x=1 if the amine A) bears a tertiary amine function and 0 if such a tertiary amine function is absent,
z=1 if a secondary amine function is present at the same time as the primary amine function in the amine compound A) and z=0 if a secondary amine function is absent,
n: initial functionality of said acrylate B) ranging from 1 to 6, preferably from 1 to 4,
y: number of aminoacrylate groups created by addition reactions of an N—H of said amine compound A) on an acrylate group of said acrylate B), with 'y' ranging from 1 to 6, preferably from 1 to 4, and n-y: from 0 to 3 and preferably from 0 to 2, represents the number of residual acrylate groups in said oligomer P.

The choice of the amine A) may condition the choice of the acrylate B). According to a first particular option, said amine compound A) is an amine compound according to A1) as defined according to the invention above and said acrylate compound B) comprises at least one multifunctional acrylate compound according to B1) and at least one monofunctional acrylate compound according to B2) and preferably said multifunctional acrylate compound according to B1) is a partial or complete multifunctional ester of at least one polyether polyol or of at least one polyol derived from said polyether with acrylic acid and said monofunctional acrylate compound according to B2) is a monoester of acrylic acid with at least one polyether diol or monool or of at least one diol or monool derived from said polyether, said polyethers more particularly being polyoxyethylenes and having a number-average molecular weight Mn of less than 2000 and preferably less than 1000. The Mn is calculated as set out above on the basis of the OH number and the functionality of said polyether polyols or monools.

According to a second particular option, said amine compound A) is an amine compound according to A2) as defined according to the claim above and preferably said acrylate compound B) is a multifunctional acrylate compound according to B1) selected from partial or complete acrylic acid esters of a polyether polyol or of a polyol derived from said polyether, or from urethane acrylates from a polyether polyol, or from epoxy acrylates from a glycidyl polyether, said polyethers more particularly being polyoxyethylenes and having a number-average molecular weight Mn of less than 2000 and preferably less than 1000. The Mn is calculated as set out above on the basis of the OH number and the functionality of said polyether polyols or monools.

More particularly, the functionality of said polyols as a basis of said multifunctional acrylates according to B1) can range from 2 to 6 and preferably from 2 to 4. The number of ethoxy units per hydroxyl function of said polyol for the ethoxylated polyols can range from 2 to 20 and preferably from 3 to 20 and more preferentially from 5 to 20.

The urethane acrylates according to B1) from polyether polyols can be obtained by reaction of a polyether polyol, in particular of a polyoxyethylene polyol, with a monoisocyanate precondensate obtained by reaction of a hydroxyalkyl acrylate such as a hydroxyethyl acrylate (HEA) with a diisocyanate.

The epoxy acrylates according to B1), from multifunctional glycidyl polyethers (glycidyl ethers of a polyether polyol), in particular glycidyl ethers of polyoxyethylene polyols, can be obtained by reaction of said glycidyl ethers of polyether polyols (epoxidized polyethers) with acrylic acid.

As suitable examples of ethoxylated polyols for multifunctional acrylate esters according to B1) mention may be made of ethoxylated trimethylolpropane (3 OH), ethoxylated pentaerythritol (4 OH), ethoxylated di-trimethylolpropane (4 OH), ethoxylated di-pentaerythritol (6 OH), ethoxylated sorbitol (3 OH), ethoxylated polyol oligoesters, polyoxyethylene polyols, ethoxylated bisphenol A (2 OH), ethoxylated isosorbide (2 OH), ethoxylated tricyclodecanedimethanol (2 OH), ethoxylated neopentyl glycol (2 OH) or ethoxylated glycerol (3 OH). These ethoxylated polyols are perfectly suitable for obtaining, by complete or partial acrylation (as appropriate, if OH functionality of at least 3), the multifunctional acrylate esters according to B1). More particularly, the multifunctional acrylate according to B1) may be a polyethylene glycol diacrylate of variable Mn ranging from 150 to 600, ethoxylated bisphenol A diacrylate with an ethoxy-unit number ranging from 4 to 15, such as SR 349, SR 601 or SR 602 from Sartomer, or ethoxylated trimethylolpropane triacrylate with an ethoxy-unit number ranging from 3 to 20, such as SR 454, SR 499, SR 502, SR 9035 or SR 415 from Sartomer, or ethoxylated glycerol triacrylate with 3 to 15 ethoxy, such as SR 9046 from Sartomer, or ethoxylated pentaerythritol tetraacrylate with 3 to 15 ethoxy, such as SR 494 from Sartomer.

As amine compound A), the following categories may be distinguished for the amine compound according to A1), as defined above:

A11) primary monoamines, with, as examples of primary monoamines that may be suitable, the following amines: N-alkylamines such as amylamine, 2-aminopentane, 3-aminopentane, 1,2-dimethylpropylamine, hexylamine, 1,3-dimethylbutylamine, n-heptylamine, n-octylamine, 2-aminooctane, 3,3,5-trimethylcyclohexylamine, ethylamine, isopropylamine, sec-butylamine, N-alkylamines bearing hydroxyl groups, such as Alaninol, N-alkoxyamines such as 3-ethoxypropylamine, 3-(2-methoxyethoxy)propylamine, 3-butoxypropylamine, 3-(2-ethylhexyloxy)propylamine, 3-isopropoxypropylamine (IPOPA), 3-methoxypropylamine (MOPA), polyether amines such as Jeffamine® M600, M1000 sold by Hunstman, amines bearing specific functions, such as 1-(2-aminoethyl)-2-imidazolidinone, also known as UDETA (urea diethylene triamine), amide-amine compounds (from a diacid and a primary diamine in excess) or ester-amide amine compounds (from an acid ester with a primary diamine in excess), A12) primary-secondary diamines, with as suitable examples, N-alkylaminoalkylamines such as N-methyl-1,3-diaminopropane, N-propyl-1,3-propanediamine, N-isopropyl-1,3-propanediamine, N-cyclohexyl-1,3-propanediamine, triacetone diamine, 1,2-diaminocyclohexane (1,2-DACH), bis(4-aminocyclohexyl)methane (PACM) or N-alkylaminoalkylamines bearing hydroxyl groups, in particular hydroxyalkyl aminoalkylamines, such as 2-(3-aminopropylamino)ethanol, A13) primary-primary diamines, with as suitable examples that may be mentioned: alkylenediamines or cycloalkylenediamines such as 1,3-bis(aminomethyl)cyclohexane (1,3-BAC), isophorone diamine (IPDA) or polyether diamines with 2 to 20 ether units, in particular ethoxy and/or propoxy units, such as the Jeffamines® sold by Hunstman under the trade names D230, D400, ED600, ED900, EDR148, EDR 176, EDR 104, THF 100, THF 140, THF 230 and RFD 270, or the fatty amines derived from $C_{36}$ fatty acid dimers as sold by Croda under the trade name Priamines®, A14) primary-tertiary diamines, with as suitable examples that may be mentioned: N,N dialkylaminoalkylamines such as diethylaminopropylamine (DEAPA), dimethylaminopropylamine (DMAPA), 3-(dibutylamino)propylamine, N,N-dimethylethylenediamine or 1-(3-aminopropyl)-2-pyrrolidine, 3-morpholinopropylamine, 1-(3-aminopropyl)piperidine, 1-(3-aminopropyl)-2-pipecoline, N,N dialkylaminoalkylamines bearing hydroxyl groups, in particular dihydroxyalkyl aminoalkyl amines such as N-(aminopropyl)diethanolamine (APDEA), A15) primary-secondary-tertiary triamines, with as suitable examples that may be mentioned: N,N-dimethyldipropylenetriamine (DMAPAPA), N-aminoethylpiperazine, 3-(2-aminoethyl)aminopropylamine, bis(3-aminopropyl) amine, methylbis(3-aminopropyl)amine, N-(3-aminopropyl)-1,4-diaminobutane.

As amine compound A), the following categories may be distinguished for the amine compound according to A2), as defined above:

A21) secondary monoamines, with as suitable examples, N,N dialkylamines such as di-sec-butylamine, diamylamine, isopropylbenzylamine, dihexylamine, diethylamine, diisopropylamine, N-isopropylmethylamine, N butylmethylamine, N-sec-butylmethylamine, N-isobutylmethylamine, N-ter-butylmethylamine, N-methylpentylamine, N-hexylmethylamine, N-methylcyclohexylamine, N-heptylmethylamine, N-octylmethylamine, N-ethylmethylamine, N-ethylpropylamine, N-ethylisopropylamine, N-butylethylamine, N-sec-butylethylamine, N-ethylcyclohexylamine, N-ethylbenzylamine, N,N-dialkylamines bearing hydroxyl groups, such as 2-(ethylamino)ethanol, 2-(isopropylamino)ethanol, 2-butylaminoethanol, 2-benzylaminoethanol, 2-octylaminoethanol, 2-sec-butylaminoethanol, A22) secondary-secondary diamines, with as suitable examples to be mentioned: N,N'-dialkyl alkyldiamines such as N,N'-dimethylethylenediamine or N,N'-dialkylcycloalkylenediamines or bis(N,N'-dialkylcycloalkylene)alkylene such as the cycloaliphatic secondary diamines under the trade names JEFFLINK® 136 and 754 sold by Hunstman, A23) secondary-tertiary diamines, with as suitable examples to be mentioned, N,N,N'-trimethyl-1,3-propanediamine or epoxy-amine amino adducts.

As amine compound A), preference is given to the amine compounds according to A1) and more particularly the following amine compounds: the primary-secondary diamines according to A12), the primary-primary diamines according to A13), the primary-tertiary diamines according to A14) or the primary-secondary-tertiary triamines according to A15) and even more particularly the diamines according to A13) or according to A14) and the triamines according to A15). According to one more particular option, said amine compound A) is according to A1) and chosen according to A14).

Regarding the functionality of said oligomer, it preferably bears, as ethylenic unsaturation, acrylate groups with a functionality with respect to acrylate groups, including ammonium acrylate if acrylic acid is used as carboxylic acid compound C), ranging from 1 to 6, preferably from 1 to 4, more preferentially from 1 to 3. More particularly, said oligomer according to the invention bears at least 2 acrylate groups per oligomer and is therefore more particularly crosslinkable, which on its own means that no crosslinking agent is required.

Regarding the amount of sites of tertiary amines, including aminoacrylates formed by addition of said amine compound A) on said acrylate B), which are converted into ammonium carboxylate salt, it can be represented by the amount of tertiary amine functions thus salified. Preferably, the oligomer according to the invention has an amount of salified tertiary amine functions ranging from 0.1 to 25, preferably from 0.5 to 15 mEq per g of said oligomer. Preferably, said oligomer has a number-average molecular weight Mn, calculated by the material balance, of less than 5000, preferably less than 3000.

The invention also covers the precursor oligomer P, which is a precursor of the oligomer as defined according to the invention above, in particular comprising or being an oligomer according to formula (I) as defined above.

A second subject of the invention relates to a solution of oligomer in a reactive diluent, which comprises the oligomer as defined above according to the invention and at least one reactive diluent D) selected from mono(meth)acrylates and/or multifunctional (meth)acrylates, preferably with D) being a (meth)acrylate of a polyether monool or polyol or of a derivative of polyether monool or polyol, of number-average molecular weight Mn of less than or equal to 600. This weight Mn is calculated on the basis of the $I_{OH}$ and the functionality of said monool or polyol and its functionality as set out above.

Another subject of the present invention relates to a process for preparing said oligomer as defined above according to the invention, which comprises the following successive steps:

i) preparation of said precursor oligomer P by addition of at least one amine compound A), according to A1) and/or according to A2) as defined above for A) according to the invention, on
B) an acrylate compound among:
  B1) at least one multifunctional acrylate having a functionality, in particular a number-average functionality if it is a mixture, ranging from 2 to 6 and preferably from 2 to 4, more preferentially from 2 to 3, even more preferentially of 2 when said amine compound A) is a compound according to A2) as defined above for the amine compound A) or
  a mixture of at least one multifunctional acrylate according to B1) as defined above and of at least one monofunctional acrylate according to B2), when said amine compound A) is an amine compound according to A1), as defined above for the amine compound A), this being for blocking, by the aminoacrylate formed, one of the two —NH groups of said primary amine function of said amine compound according to A1),
with the following molar ratios between groups: (acrylate)/(—NH)>1 so that at least one residual acrylate group is borne by the addition product i) corresponding to said precursor oligomer P and in the case where said amine compound A) is according to A1), said acrylate B) is a mixture of multifunctional acrylate according to B1) and of monofunctional acrylate according to B2) with a B2/A1 molar ratio=1/1;

ii) salification of said precursor oligomer P which is the product of the addition step i), in ammonium carboxylate salt form, by said carboxylic acid compound C), as defined above according to the invention, preferably with a (carboxy)/(tertiary amine) molar ratio between carboxy groups and tertiary amine functions (≡N—) including tertiary amines among aminoacrylate groups, ranging from 0.10 to 1.00, preferably from 0.5 to 1.00 and more preferentially from 0.5 to 0.99.

Also part of the invention is a polymerizable, in particular crosslinkable, oligomer as obtained by means of the process as defined above according to the invention.

Another subject of the invention relates to a polymerizable, in particular crosslinkable, composition which comprises as binder at least one oligomer, as defined above according to the invention or obtained by means of a process as defined above according to the invention, or a solution as defined above according to the present invention.

More particularly, said composition is polymerizable, in particular crosslinkable:
  by radiation, in particular UV, LED, laser or electron beam radiation, preferably UV radiation,
  thermally or by peroxide or by hydroperoxide in the presence of an accelerator,
  by a dual route combining at least two of the abovementioned routes,
and, preferably,
  by radiation, more preferentially by UV radiation.

Even more particularly, it is a question of a polymerizable, in particular crosslinkable, composition for a temporary-use material, preferably among a coating, in particular ink, varnish or adhesive, or among a hydrogel or support material for a layer-by-layer 3D printing object, more preferentially a coating or support material for a layer-by-layer 3D printing object and even more preferentially for a support material of a layer-by-layer 3D printing object.

Another subject of the present invention relates to the use of an oligomer as defined above according to the invention or of a solution of oligomer as defined according to the invention or to the use of the oligomer obtained by means of a process as defined according to the invention, as a polymerizable, and in particular crosslinkable, binder, which is optionally water-soluble, in compositions which are polymerizable and in particular crosslinkable, preferably under radiation. Said use applies in particular to a temporary-use material which can be removed by washing with water alone or with salt water or with another aqueous solution, preferably having a pH>7, more preferentially >8, in particular to temporary-use materials among coatings, hydrogels or a support material for a layer-by-layer 3D printing object, more particularly coatings or support materials for a layer-by-layer 3D printing object.

Even more particularly, said use applies specifically to the printing of 3D objects by polymerization, in particular crosslinking, under radiation layer by layer, of a composition comprising said oligomer or said solution of oligomer, as temporary-use material for support or consolidation or molding of said final 3D object, obtained after removal of said temporary-use material by washing with water or with a saline solution or with another aqueous solution.

Another possibility for use relates to hydrogels obtained from the crosslinking of a crosslinkable composition comprising said oligomer or said solution of oligomer, followed by swelling with water or a suitable aqueous solution. Such a use can in particular relate to the transport of pharmaceutical or phytosanitary active ingredients or active ingredients for wood treatment using said hydrogels as carrier or vector of said pharmaceutical or phytosanitary active ingredient or active ingredient for wood treatment.

Finally, also part of the present invention is a polymeric, in particular crosslinked, material which results from the use, as polymerizable, in particular crosslinkable, binder, of at least one oligomer according to the invention as defined above or of an oligomer obtained by means of the process of the invention as defined above or of a solution of oligomer according to the invention as defined above, or from the polymerization, in particular from the crosslinking, of a polymerizable, in particular crosslinkable, composition according to the invention, as defined above.

More particularly, said material is a temporary-use material, which can be removed by water, a saline solution or another aqueous solution suitable for this removal, for example by adjusting the pH to >7, in particular adjusting the pH to >8, preferably among coatings, hydrogels or a support or consolidation or molding material for an object which is 3D-printed layer-by-layer under radiation and more preferentially a temporary support or consolidation or molding material for an object which is 3D-printed layer-by-layer under radiation.

The examples that follow are presented to illustrate the invention and its performance qualities and do not in any way limit its scope.

EXAMPLES

1) Preparation and Formulation of Oligomers According to the Invention

Example 1

108.54 g of dimethylaminopropylamine (DMAPA from Huntsman, Mw of 102.18 g/mol) and 0.14 g of 2,6-di-tert-butyl-4-methylphenol (BHT) are introduced into a 1 l reactor. 356.93 g of polyethylene glycol monoacrylate (Bisomer PEA6 from Geo Specialty Chemicals, Mw of 336 g/mol) are added, with stirring and bubbling of air, at ambient temperature, over the course of one hour at constant flow rate. An exothermy of approximately 20° C. is observed. At the end of the addition, the temperature of the mixture is brought to 60° C. After four hours at 60° C., 464.22 g of butanediol diglycidyl ether diacrylate (BDDGEDA, CN132 from Sartomer, Mw of 256.8 g/mol) are added to the mixture over the course of 30 minutes at constant flow rate. At the end of the addition, the temperature of the mixture is maintained at 60° C. for three hours, then 70.17 g of glutaric acid (Aldrich, 132.11 g/mol) are added to the mixture. At the end of the addition, reaction is carried out for a further period of one hour at 60° C., before recovering the final product.

Example 2

125.68 g of dimethylaminopropylamine (DMAPA from Huntsman, Mw of 102.18 g/mol) and 0.93 g of 2,6-di-tert-butyl-4-methylphenol (BHT) are introduced into a 1 l reactor. 413.27 g of polyethylene glycol monoacrylate (Bisomer PEA6 from Geo Specialty Chemicals, Mw of 336 g/mol) are added, with stirring and bubbling of air, at ambient temperature, over the course of one hour at constant flow rate. An exothermy of approximately 20° C. is observed. At the end of the addition, the temperature of the mixture is brought to 60° C. After four hours at 60° C., 371.45 g of polyethylene glycol diacrylate (SR259 from Sartomer, Mw of 302 g/mol) are added to the mixture over the course of 30 minutes at constant flow rate. At the end of the addition, the temperature of the mixture is maintained at 60° C. for three hours, then 88.68 g of acrylic acid (Arkema, Mw of 72.1 g/mol) are added.

At the end of the addition, reaction is carried out for a further period of one hour at 60° C., before recovering the final product.

Example 3

131.16 g of dimethylaminopropylamine (DMAPA from Huntsman, Mw of 102.18 g/mol) and 1.01 g of 2,6-di-tert-butyl-4-methylphenol (BHT) are introduced into a 1 l reactor. 775.29 g of polyethylene glycol diacrylate (SR259 from Sartomer, Mw of 302 g/mol) are added, with stirring and bubbling of air, at ambient temperature, over the course of one hour at constant flow rate. An exothermy of approximately 20° C. is observed. At the end of the addition, the temperature of the mixture is brought to 60° C. After four hours at 60° C., 92.55 g of acrylic acid (Arkema, Mw of 72.1 g/mol) are added over the course of 30 minutes at constant flow rate. At the end of the addition, reaction is carried out for a further period of one hour at 60° C., before recovering the final product.

Example 4

80.89 g of dimethylaminopropylamine (DMAPA from Huntsman, Mw of 102.18 g/mol) and 0.831 g of 2,6-di-tert-butyl-4-methylphenol (BHT) are introduced into a 1 l reactor. 554.13 g of polyethylene glycol monoacrylate (Bisomer PEA5 from Geo Specialty Chemicals, Mw of 336 g/mol) are added, with stirring and bubbling of air, at ambient temperature, over the course of one hour at constant flow rate. An exothermy of approximately 20° C. is observed. At the end of the addition, the temperature of the mixture is brought to 60° C. After four hours at 60° C., 114.15 g of acrylic acid (Arkema, Mw of 72.1 g/mol) are added to the mixture over the course of 30 minutes at constant flow rate. At the end of the addition, reaction is carried out for a period of one hour at 60° C. 250 g of polyethylene glycol diacrylate (SR 344 from Sartomer) as dilution monomer or reactive diluent are then added. Homogenization is carried out for a further period of 30 minutes at 60° C., before recovering the final product.

2) Comparative Examples

As comparison reference, use is made of crosslinkable compositions representative of the prior art, comprising, in addition to the reactive components without aminoacrylates, water-soluble non-reactive components such as polyethylene glycol 600 (PEG 600).

Example 5

626 g of polyethylene glycol 600, 368 g of polyethylene glycol 600 diacrylate (SR 610 from Sartomer) and 6 g of propoxylated glyceryl triacrylate (SR 9020 from Sartomer) are introduced into a 1 l reactor. The mixture is brought to 60° C. with stirring and bubbling of air. The mixing time is 30 minutes at 60° C.

Example 6

337 g of polyethylene glycol 600, 342 g of polyethylene glycol 600 diacrylate (SR 610 from Sartomer), 315 g of polyethylene glycol monoacrylate (Bisomer PEA6 from Geo Specialty Chemicals, Mw of 336 g/mol) and 6 g of propoxylated glyceryl triacrylate are introduced into a 1 l reactor. The mixture is brought to 60° C. with stirring and bubbling of air. The mixing time is 30 minutes at 60° C.

3) Characteristics of the Compositions Before Crosslinking

TABLE 1

| Characteristics | Unit | Compositions according to the invention (produced as described in examples 1 to 4). | | | | Comparative compositions | |
|---|---|---|---|---|---|---|---|
| | | 1 | 2 | 3 | 4 | 5 | 6 |
| Brookfield Viscosity at 25° C. | mPa · s | 40 000 | 2091 | 1636 | 11 360 | 150-200 | 150-200 |
| Brookfield Viscosity at 90° C. | mPa · s | 1020 | 52 | 43 | 38 | 10-15 | 10-15 |

4) Evaluation of the Properties of the Crosslinked Compositions and Water-Fragmentation Performances in an Aqueous Solution For the compression and water-fragmentation tests, the products as described according to the invention (examples 3 and 4) and the comparative compositions (examples 5 and 6) are formulated with an overall photoinitiator content of 5% by weight, composed of 4% of Irgacur® 1173 (BASF) and of 1% by weight of Lucirin® TPO-L (BASF) for 95% by weight of tested composition of table 1. The crosslinking is carried out under a 120 Watt/cm UV lamp. lamp are required in order to obtain the crosslinked object. The results are presented in table 3 below:

TABLE 3

|  | Unit | Composition according to the invention | | Comparative composition | |
| --- | --- | --- | --- | --- | --- |
|  |  | Example 3 | Example 4 | Example 5 | Example 6 |
| Weight of object before test | g | 15.6 | 15.0 | 14.8 | 14.7 |
| "Residual" solid fraction filtered through filter paper | g | 7.8* | 5.25** | 14.69*** | 12.5*** |
| Fraction passing into the aqueous phase and through the standard filter paper | % | 50 | 65 | 1 | 15 |
| Degree of "water-fragmentability" |  | 4-5 | 5 | 0 | 2 |

*particles of homogeneous size with maximum size less than 7 mm
**particles of homogeneous size with maximum size less than 5 mm
***particles of very variable (very heterogeneous) size of predominant maximum size greater than 20 mm Compression Test (According to Standard NF EN ISO 604)
Type of test specimens: Cylindrical (diameter: 13.3 mm, height 26.5 mm) obtained by crosslinking, under a 120 Watt/cm UV lamp, of a composition contained in a sacrificed cylindrical glass mold having the dimensions (diameter) corresponding to those of the test specimen (length adjusted by cutting the crosslinked object).
Testing machine: INSTRON 1185 ReNew,10 kN cell
Test speed: 1.3 mm/min.
The test specimens were tested at 23° C.
The results are presented in table 2 below:

TABLE 2

| Characteristic | Unit | Composition according to the invention | | Comparative composition | |
| --- | --- | --- | --- | --- | --- |
|  |  | Example 3 | Example 4 | Example 5 | Example 6 |
| Young's modulus | MPa | 7.437 | 3.548 | 0.695 | 2.489 |

Water-Fragmentation Test
The water-fragmentation test is defined in the following way:
A bulk-crosslinked object in the form of a cylinder of 15 g and of 15 cm$^3$ (2 cm in height, 1.5 cm in radius) is immersed for two hours in a bath containing 400 ml of an aqueous solution of sodium hydrogen carbonate (pH>7) at 60° C., with magnetic stirring (magnetic stirrer bar). After two hours of treatment, the mixture is filtered and the residual solids are dried.
Two criteria are then measured and evaluated:
1) The weight of the cylinder before the test, then after filtration and drying, indicates the part of the object that has gone into solution, "water-soluble" or "water-dispersible".
2) The appearance of the cylinder after the test: a score of 0 to 5 is attributed; it indicates the degree of "water-fragmentability" of the material.
   a. 0: the original cylinder has remained intact
   b. 5: the cylinder is completely fragmented, the residual solids are in the form of homogeneous powder after filtration and drying.

The cylindrical objects prepared for the test are obtained using a Teflon mold. 20 passes under a 120 Watt/cm UV Additional Examples of Oligomers Example 7

808.66 g of methoxy polyethylene glycol monoacrylate (SR 551 from Sartomer, Mw of 404 g/mol), 0.983 g of 2,6-di-tert-butyl-4-methylphenol (BHT) and 0.983 g of methyl ether of hydroquinone (EMHQ) are introduced into a 1 l reactor. 78.80 g of dimethylaminopropylamine (DMAPA from Huntsman, Mw of 102.18 g/mol) are added, with stirring and bubbling of air, at ambient temperature over the course of 30 minutes at constant flow rate. An exothermy of approximately 10° C. is observed. At the end of the addition, the temperature of the mixture is brought to 50° C. After four hours at 50° C., 110.08 g of acrylic acid (Arkema, Mw of 72.1 g/mol) are added to the mixture over the course of thirty minutes at constant flow rate. The reaction is strongly exothermic; the flow rate of the addition is adjusted in order not to exceed the temperature of 55° C. in the medium. At the end of the addition, reaction for two hours at 50° C. is carried out. After two hours at 50° C., 0.494 g of phenothiazine is added to the mixture.

Example 8

791.77 g of methoxy polyethylene glycol monoacrylate (SR 551 from Sartomer, Mw of 404 g/mol), 0.964 g of 2,6-di-tert-butyl-4-methylphenol (BHT) and 0.964 g of methyl ether of hydroquinone (EMHQ) are introduced into a 1 l reactor. 98.19 g of dimethylaminopropylamine (DMAPA from Huntsman, Mw of 102.18 g/mol) are added, with stirring and bubbling of air, at ambient temperature over the course of 30 minutes at constant flow rate. An exothermy of approximately 10° C. is observed. At the end of the addition, the temperature of the mixture is brought to 50° C. After four hours at 50° C., 107.63 g of acrylic acid (Arkema, Mw of 72.1 g/mol) are added to the mixture over the course of thirty minutes at constant flow rate. The reaction is strongly exothermic; the flow rate of the addition is adjusted in order not to exceed the temperature of 55° C. in the medium. At the end of the addition, reaction for two hours at 50° C. is carried out. After two hours at 50° C., 0.482 g of phenothiazine is added to the mixture.

Example 9

388.40 g of tert-butyl cyclohexanol acrylate (SR 217 from Sartomer, Mw of 210/mol), 0.98 g methyl ether of hydroquinone (EMHQ) and 0.98 g of 2,6-di-tert-butyl-4-methylphenol (BHT) are introduced into a 1 l reactor. 147.67 g of dimethylaminopropylaminopropylamine (DMAPAPA from Aldrich, Mw of 159.27 g/mol) are added, with stirring and bubbling of air, at ambient temperature, over the course of one hour at constant flow rate. An exothermy of approximately 10° C. is observed. At the end of the addition, the temperature of the mixture is brought to 50° C. After four hours at 50° C., 280 g of polyethylene glycol diacrylate (SR 259 from Sartomer, Mw of 302 g/mol) are added over the course of one hour at constant flow rate. After two hours at 50° C., 180.48 g of acrylic acid (Arkema, Mw of 72.1 g/mol) are added to the mixture over the course of 30 minutes at constant flow rate. The introduction flow rate is adjusted in order not to exceed a temperature of 55° C. in the medium. At the end of the addition, reaction for two hours at 50° C. is carried out. After two hours at 50° C., 0.49 g of phenothiazine is added to the mixture.

TABLE 4

Characteristics of the products of examples 7 to 9

| Characteristics | Unit | Example 7 | Example 8 | Example 9 |
|---|---|---|---|---|
| Brookfield Viscosity at 25° C. | mPa · s | 353 | 147 | 35 600 |
| Brookfield Viscosity at 85° C. | mPa · s | 19.0 | 15.8 | 836 |
| Young's Modulus | MPa · s | 1.0* | 0.7* | 3.5 |

*Measurements carried out with: 20% of SR 344 (Polyethylene Glycol 400 Diacrylate from Sartomer)

The invention claimed is:

1. A polymerizable oligomer bearing at least one ethylenic unsaturation and at least one ammonium carboxylate ionic bond and comprising in its structure:
   P) at least one precursor oligomer bearing at least one tertiary amine function in the form of an aminoacrylate group resulting from the addition of A) at least one amine compound A1) bearing at least one primary amine function (—NH$_2$) and/or secondary amine function (—NH) and optionally at least one tertiary amine function and/or A2) bearing at least one secondary amine function (—NH) and optionally at least one tertiary amine function, on B) at least one hydrophilic acrylate compound with as a result the formation of said at least one aminoacrylate group, and
   C) at least one carboxylic acid compound attached to said precursor oligomer P by at least one ammonium carboxylate ionic bond with at least one of said aminoacrylate groups and optionally at least one of said tertiary amine functions of said amine compound A).

2. The oligomer of claim 1, wherein said amine compound A) is selected from at least one of:
   A1) an amine compound bearing at least one primary amine function, and optionally at least one tertiary amine function or at least one secondary amine function or both, or
   A2) an amine compound bearing at least one secondary amine function, and optionally at least one tertiary amine function,
and wherein said acrylate compound B) is at least one multifunctional acrylate compound B1) or at least one monofunctional acrylate compound B2) or both.

3. The oligomer of claim 2, wherein said hydrophilic acrylate compound B) is a mixture of the multifunctional acrylate compound B1) and of the monofunctional acrylate compound B2).

4. The oligomer of claim 1, wherein said aminoacrylate group can bear at least one ethylenic unsaturation or no ethylenic unsaturation and, in the latter case, said acid compound C) is ethylenically unsaturated.

5. The oligomer of claim 1, wherein said acid compound C) is a monoacid C1) which is ethylenically unsaturated C11) and said oligomer bears at least two ammonium carboxylate ionic bonds.

6. The oligomer of claim 1, wherein:
   when said carboxylic acid compound C) is a monoacid C1), in this case: C1) is an ethylenically unsaturated monoacid C11) and at least one ethylenic unsaturation of said oligomer is borne by at least said monoacid C11) by ammonium carboxylate bonding with at least one of said tertiary amine functions among said aminoacrylate groups or optionally among the tertiary amine functions borne by said amine compound A) and optionally at least one other ethylenic unsaturation of said oligomer is borne by at least one aminoacrylate group in the form of an aminoacrylate-end acrylate group of said precursor oligomer P or
   C1) is a saturated monoacid C12) and at least one ethylenic unsaturation of said oligomer is borne by at least one aminoacrylate group in the form of an aminoacrylate-end acrylate group of said precursor oligomer P, said monoacid C1) preferably being an unsaturated monoacid C11) and
   when said carboxylic acid compound C) is a polycarboxylic acid C2), in this case:
   C2) is an ethylenically unsaturated polyacid C21) and at least one ethylenic unsaturation of said oligomer is borne by at least said polyacid C21) and optionally, in addition, at least one ethylenic unsaturation is borne by at least one aminoacrylate group in the form of aminoacrylate-end acrylate groups of said precursor oligomer P or
   C2) is a polyacid C22) which is saturated and said precursor oligomer P bears at least one aminoacrylate-end acrylate group and said resulting oligomer bears at least two acrylate ethylenic unsaturations.

7. The oligomer of claim 6, wherein said carboxylic acid compound C) is an unsaturated diacid C21) or a saturated diacid C22) linking, by two carboxylic ionic bonds, two molecules of said precursor oligomer P, by salification in ammonium carboxylate salt form of one of said tertiary amine functions among said aminoacrylate groups formed, or optionally among said tertiary amine functions of said amine compound A), on each of said molecules of said oligomer P or in that said carboxylic acid compound C) is a monoacid C1), which is an ethylenically unsaturated monoacid C11) and has a polymerizable ethylenic unsaturation, and said monoacid C11) salifies at least two of said tertiary amine functions in ammonium carboxylate form.

8. The oligomer of claim 1, wherein said precursor oligomer P comprises, in its structure, hydrophilic chain segments selected from polyethers or from polyesters or from polyurethanes based on oligoether polyols or on ethoxylated polyols, said segments having a number-average molecular weight Mn of less than 2000.

9. The oligomer of claim 1, wherein said carboxylic acid compound C) is an ethylenically unsaturated monoacid C11) and selected from: acrylic or methacrylic acid, crotonic acid (trans-2-butenoic acid) or β-carboxyethyl acrylate (β-CEA) or mixtures thereof.

10. The oligomer of claim 1, wherein said carboxylic acid compound C) a saturated dicarboxylic acid C22) and selected from: succinic acid, malonic acid, malic acid, glutaric acid ($C_5$: bearing 5 carbon atoms), adipic acid ($C_6$), pimelic acid ($C_7$) or acid diesters of abovementioned diacids with a $C_2$ to $C_4$ alkanediol or with a di-, tri- or tetraethylene glycol or diacids among fatty acid dimers and/or trimers.

11. The oligomer of claim 1, wherein said carboxylic acid compound C) is an unsaturated dicarboxylic acid C21) and selected from: itaconic acid, maleic acid, fumaric acid, tetrahydrophthalic acid (cyclohexenedioic acid), or acid diesters of the abovementioned diacids with a $C_2$ to $C_4$ alkanediol or with a di-, tri- or tetraethylene glycol or non-hydrogenated fatty acid dimers and/or trimers ($C_{36}$ dimers and $C_{54}$ trimers), or mixtures thereof.

12. The oligomer of claim 1, wherein at least one of said amine compound A) is a mixture of amine compounds A), said acrylate compound B) is a mixture of compounds B), or said acid compound C) is a mixture of compounds C).

13. The oligomer of claim 1, wherein said amine compound A) is an amine compound A1) and said acrylate compound B) comprises at least one multifunctional acrylate compound B1) and at least one monofunctional acrylate compound B2).

14. The oligomer of claim 1, wherein said amine compound A) is an amine compound A2) and said acrylate compound B) is a multifunctional acrylate compound at least one multifunctional acrylate compound B1) selected from partial or complete acrylic acid esters of a polyether polyol or of a polyol derived from said polyether, or from urethane acrylates from a polyether polyol, or from epoxy acrylates from a glycidyl polyether.

15. The oligomer of claim 1, wherein said oligomer has a functionality with respect to acrylate groups, including ammonium acrylate if acrylic acid is used as carboxylic acid compound C), of from 1 to 6.

16. The oligomer of claim 1, wherein the oligomer has an amount of salified tertiary amine function ranging from 0.1 to 25 mEq per g of said oligomer.

17. A solution of oligomer in a reactive diluent comprising the oligomer of claim 1 and at least one reactive diluent D) selected from at least one of mono(meth)acrylates or multifunctional (meth)acrylates.

18. A process for preparing an oligomer of claim 1, comprising the following successive steps:
i) preparation of said precursor oligomer P by addition of at least one amine compound A), according to A1) or according to A2) or both, on B) an acrylate compound from:
   B1) at least one multifunctional acrylate having a functionality ranging from 2 to 6 when said amine compound A) is a compound A2) or
   a mixture of at least one multifunctional acrylate according to B1) and of at least one monofunctional acrylate B2), when said amine compound A) is an amine compound A1), this being for blocking, by the aminoacrylate formed, one of the two —NH groups of said primary amine function of said amine compound according to A1),
with the following molar ratios between groups:
(acrylate)/(—NH)>1 so that at least one residual acrylate group is borne by the addition product i), which is said precursor oligomer P,
and in the case where said amine compound A) is A1) and said acrylate B) is a mixture of multifunctional acrylate B1) and of monofunctional acrylate B2) with a B2/A1 molar ratio=1/1,
ii) salification of said precursor oligomer P which is the product of the addition step i), in ammonium carboxylate salt form, by said carboxylic acid compound C) with a (carboxy)/(tertiary amine) molar ratio between carboxy groups and tertiary amine functions (=N—) including tertiary amines among aminoacrylate groups, ranging from 0.10 to 1.00.

19. A polymerizable oligomer, obtained by the process of claim 18.

20. A polymerizable composition comprising, as binder, at least one oligomer of claim 1.

21. The composition of claim 20, polymerizable:
by radiation selected from UV, LED, laser or electron beam radiation,
thermally or by peroxide or by hydroperoxide in the presence of an accelerator,
or by a dual route combining at least two of the abovementioned routes.

22. The composition of claim 20, wherein the composition is for a temporary-use material, among a coating or among a hydrogel or support material for a layer-by-layer 3D printing object.

23. A method of preparing a material by curing the oligomer of claim 1 under radiation.

24. The method of claim 23, wherein the material can be removed by washing with water alone or with salt water or with another aqueous solution having a pH>7 which temporary-use material is selected among coatings, hydrogels or a support material for a layer-by-layer 3D printing object.

25. The method of claim 23, wherein the method applies to the printing of 3D objects by polymerization under radiation layer by layer, of a composition comprising said oligomer as temporary-use material for support or consolidation or molding of said final 3D object, obtained after removal of said temporary-use material by washing with water or with a saline solution or with another aqueous solution.

26. A polymeric material obtained by polymerizing the composition of claim 20.

* * * * *